United States Patent
Lopez Gil et al.

(10) Patent No.: US 12,232,811 B2
(45) Date of Patent: Feb. 25, 2025

(54) COMPUTER-IMPLEMENTED METHOD AND SYSTEM FOR INTERACTIVELY MEASURING OCULAR REFRACTIVE ERRORS, ADDITION AND POWER OF READING GLASSES

(71) Applicant: VISIONAPP SOLUTIONS S.L., Aguilas (ES)

(72) Inventors: Norberto Lopez Gil, Aguilas (ES); Arthur Bradley, Aguilas (ES); Mateusz Tomasz Jaskulski, Aguilas (ES)

(73) Assignee: VISIONAPP SOLUTIONS S.L., Aguilas (ES)

( * ) Notice: Subject to any disclaimer, the term of this patent is extended or adjusted under 35 U.S.C. 154(b) by 629 days.

(21) Appl. No.: 17/598,391

(22) PCT Filed: Apr. 21, 2020

(86) PCT No.: PCT/EP2020/061054
§ 371 (c)(1),
(2) Date: Sep. 27, 2021

(87) PCT Pub. No.: WO2020/216732
PCT Pub. Date: Oct. 29, 2020

(65) Prior Publication Data
US 2022/0151488 A1      May 19, 2022

(30) Foreign Application Priority Data

Apr. 25, 2019   (EP) .................................... 19382316

(51) Int. Cl.
*A61B 3/103*   (2006.01)
*A61B 3/00*    (2006.01)
*G06V 40/16*   (2022.01)

(52) U.S. Cl.
CPC .......... *A61B 3/1035* (2013.01); *A61B 3/0033* (2013.01); *G06V 40/178* (2022.01)

(58) Field of Classification Search
CPC ..... A61B 3/0033; A61B 3/103; A61B 3/1035; G06V 40/178
See application file for complete search history.

(56) References Cited

U.S. PATENT DOCUMENTS

2017/0079523 A1   3/2017   Limon
2018/0125352 A1   5/2018   Schmid et al.

OTHER PUBLICATIONS

International Search Report and Written Opinion For Corresponding International Application No. PCT/EP2020/061054, 10 Pages, Jul. 8, 2020.

*Primary Examiner* — Jack Dinh
(74) *Attorney, Agent, or Firm* — Lucas & Mercanti, LLP

(57) ABSTRACT

A system and method for interactively measuring ocular refractive errors, addition and power of reading glasses without the need of an optical component that would change optical vergence of a target. The system can measure the distance from a user's eyes to either or both border of interval of clear vision, for one orientation or two perpendicular orientations. The measurements together with the user's age can be used to estimate sphero-cylindrical refraction, addition and power of reading glasses. The system can use different sizes, directions and colors of targets which can change with said distance or user interaction.

17 Claims, 5 Drawing Sheets

330a  330b  330c  330d 330e  330f  330g  330h

COMPUTER-IMPLEMENTED METHOD AND SYSTEM FOR INTERACTIVELY MEASURING OCULAR REFRACTIVE ERRORS, ADDITION AND POWER OF READING GLASSES

CROSS REFERENCE TO RELATED APPLICATION

This application is a 371 of PCT/EP2020/061054, filed Apr. 21, 2020, which claims the benefit of European Patent Application No. 19382316.8 filed Apr. 25, 2019, each of which are incorporated herein by reference.

FIELD OF THE INVENTION

This is related to the fields of optometry, visual optics, physiological optics, electronics and computers. In particular, this is related to systems and methods of measure the near point and far points of a human eye and its focusing errors, which can result in myopia, hyperopia, astigmatism and presbyopia.

BACKGROUND OF THE INVENTION

A perfect eye forms images of infinitely distant objects precisely on the retina. The far point (FP) of a perfect eye is thus located at infinity. As the distance between the eye and an object becomes shorter, the eye maintains the object in focus by means of accommodation, which is a process where, primarily, the curvature of a crystalline lens inside the eye changes. Once a minimum distance of accommodation is reached and the lens cannot become any more curved, an object is located at the eye's near point (NP). In optometry, distances are often expressed in units of diopters (D), which are the inverse of meters (m). The dioptric distance between FP and NP of an eye is called the amplitude of accommodation (AA). Since the FP of a perfect eye is located at infinity, it corresponds to 0 D. A NP of a perfect eye can, for example, be located at a distance of 0.1 m, which corresponds to 10 D. In this case AA is 10 D.

Real eyes suffer from aging, and people who are approximately 45 and older suffer from presbyopia—a condition where the crystalline lens of the eye loses the ability to change shape. The amplitude of accommodation of real eyes drops with age from approximately 20 D in infancy to 0 D in late adulthood when the eye loses the ability to form clear images of near objects on the retina. There are many reports documenting the relationship between age and maximum change in accommodation in human eyes [1][2].

Furthermore, real eyes suffer from focusing errors caused by optical imperfections in their refractive surfaces (cornea and crystalline lens) and/or from a mismatch between the refractive power and the axial length of the eye, which are called refractive errors. Such errors, which cause the far point to be located closer than at infinity (myopia) or further away than infinity (hyperopia) prevent the eye from forming images precisely on the retina and result in deterioration of visual quality and require optical correction.

Refractive errors which can be corrected by means of spectacles, contact lenses, intraocular lenses, or refractive surgery can be divided into spherical errors (myopia or hyperopia), cylindrical errors (astigmatism) and presbyopia. Astigmatism is a condition where the optical power of the eye varies with meridian (orientation) causing the far point to split into two (meridians); one corresponding to, for example, horizontal, and the other corresponding to vertical components of the image. This causes the visual quality of images of vertical objects (for example a fence) to be different from the visual quality of images of horizontal objects (for example a striped dress) and can give rise to nausea, seeing double images, and a general loss of vision quality. Many authors have shown that astigmatism magnitude and axis do not change very much during accommodation [3][4].

The fact that astigmatism can be present both in a relaxed and accommodated eyes means that both the FP and the NP can each be split. Each can correspond to two distances depending on the orientation of the object; distal far point (dFP) and proximal far point (pFP), and distal near point (dNP) and proximal near point (pNP) for FP and NP, respectively. These four distances correspond to the borders of the interval of clear vision (BICV).

Due to the light dispersion of the ocular media, which is a function of wavelength, positions of FP and NP depend on the spectral composition (color) of the object [5] imaged by the optics of the eye onto the retina. For example, in the case of a 2 D myope looking at an object on a black background, a FP can be located at a distance of 0.5 m, 0.4 m, and 0.53 m for white, blue and red objects, respectively. Eye dispersion is known and similar between subjects, so FP and NP for any given wavelength (color) can be calculated [6].

Prior to its correction, the type and amount of refractive error must be determined by means of a procedure known as refraction, which consists of finding the combination of spherical and cylindrical lenses which correct the focusing errors of the eye described above. Refraction is performed either using dedicated optical instruments, which can measure light exiting the eye (objective refraction), or by trained clinicians using a chart and a set of trial lenses (subjective refraction).

Perfect focus is never achieved by the human eye even after sphero-cylindrical correction due to the presence of high-order monochromatic aberrations [7] and well documented errors in both objective and clinician determined subjective refractions [8,9]. Moreover, optimal refractions can also vary with task and the object being viewed [10]. For instance, if the goal of the refraction is to read optotypes or letters, it will depend on letter size. Low myopes can be able to read large letters without correction but need a correction for small letters. Similarly, low presbyopes can read medium- or large-size fonts but are unable to read small print. Thus, the position of FP and NP depends both on object size [11] and subject's refraction.

Numerous patents and patent applications regarding systems and methods for measuring ocular refractive errors have been proposed. Some include techniques to find cylindrical lenses that correct ocular astigmatism [12]. However, they are all related to obtaining the measurements at the FP of an eye. Moreover, these patents and applications are based on the use of optical systems to modify optical vergence in images of objects, and not on changing the real, physical distance from said objects. Furthermore, they do not include changes in object size (e.g. size of target on a screen) depending on said distance, which is required for the size of an image formed by the optics of the eye to be distance-independent.

To the best of the authors' knowledge there are no previously published patent applications related to systems and methods for interactively measuring ocular refractive errors and power and addition of reading glasses based on measurements of distance between a subject's head and a device, where there is continuous change of object size, and where a subject can interactively choose one of the BICV according to subjective preference. Such systems can be implemented in modern electronic devices which include screens, cameras, sensors and processors.

REFERENCES

1. Duane A. Studies in Monocular and Binocular Accommodation, with Their Clinical Application. Transactions of the American Ophthalmological Society. 1922; 20:132-57.
2. Jackson E. Amplitude of Accommodation at Different Periods of Life. California state journal of medicine. 1907; 5(7):163-6.
3. Borish I M. Clinical refraction, 3rd ed. Chicago: Professional Press, 1970.
4. Bannon R E. A study of astigmatism at the near point with special reference to astigmatic accommodation. Am J Optom Arch Am Acad Optom. 1946; 23:53-75.
5. Sivak J G, Mandelman T. Chromatic dispersion of the ocular media. Vision Res 1982; 22:997-1003.
6. Thibos L N, Ye M, Zhang X, Bradley A. The chromatic eye: a new reduced-eye model of ocular chromatic aberration in humans. Appl Opt 1992; 31:3594-3600.
7. Charman W N. Wavefront aberration of the eye: a review. Optom Vis Sci 1991; 68:574-583.
8. Bullimore, M. A., Boyd, T., Mather, H. E., & Gilmartin, B. (1988). Near retinoscopy and refractive error. *Clinical and Experimental Optometry,* 71(4), 114-118.
9. Bullimore, M. A., Fusaro, R. E., & Adams, C. W. (1998). The repeatability of automated and clinician refraction. *Optometry and vision science: official publication of the American Academy of Optometry,* 75(8), 617-622.
10. López-Gil, N., Peixoto-de-Matos, S. C., Thibos, L. N., & González-Méijome, J. M. (2012). Shedding light on night myopia. Journal of Vision, 12 (5):4, 1-9.
11. Heath G. G. (1956). The influence of visual acuity on accommodative responses of the eye. Am. J. Opt&t. & drchs Am. Acad. Oprom. 33. 513-524.
12. Limon, Ofer. System and method for measurement of refractive error of an eye based on subjective distance metering. Patent. WO/2014/195951.

SUMMARY OF THE INVENTION

The present invention refers to computer-implemented systems and methods for interactively measuring ocular refractive errors, addition and power of reading glasses. The methods are based on interactive, subjective measurements of distance between a subject's head and an electronic device corresponding to either of the BICV.

The system proposed herein can include the following components of an electronic device:
  a. Distance measurement circuitry, which can include passive components such as one or more cameras, or active components such as emitters, detectors, or others, or any combination thereof.
  b. User interface, which can include an electronic screen with a tactile surface or a keypad or a microphone, or others, or any combination thereof.
  c. Control circuitry and processing circuitry, which can include processors, memory modules, wired or wireless connections between system modules and components and remote networks, or others, or any combination thereof.

The method proposed herein can comprise the steps of:
a. Acquiring information about a user, such as age (AGE), gender, geographic location, eye to be tested or others, or any combination thereof.
  i. According to some embodiments of the present invention, the acquiring information about a user comprises configuring a user interface module to prompt a user to input said information into a user interface.
  ii. According to some embodiments of the present invention, the acquiring information about a user comprises automatically detecting said information based on an image of a user's head from a camera included in an electronic device or other databases.
b. Displaying a target on an electronic screen such as one or more letters or optotypes, a geometrical pattern or a still or moving picture, or other, or any combination thereof.
  i. According to some embodiments of the present invention, the displaying a target on an electronic screen comprises changing the size, shape, rotation, color, background color or other characteristics or any combination of any of the above in accordance with a user interaction with an electronic device using a user interface.
  ii. According to some embodiments of the present invention, the displaying a target on an electronic screen comprises changing the size, shape, rotation, color, background color or other characteristics or any combination of any of the above with a change of distance between a user's head and an electronic device.
c. Changing the distance between a user's head and an electronic device to optimize the subjective visual quality of the target according to a criterion.
  i. According to some embodiments of the present invention, the changing the distance between a user's head and an electronic device comprises holding a device in a user's hand and bringing it closer to the user's face or further away from the face.
  ii. According to some embodiments of the present invention, the changing the distance between a user's head and an electronic device comprises situating one or more reflective surfaces, the electronic device, and changing a distance between the device and the surface or a distance between the head and the surface, or any combination thereof.
  iii. According to some embodiments of the present invention, the changing the distance between a user's head and an electronic device comprises changing the distance by a third party, such as another person, another apparatus, or other, or any combination of any of the above.
d. Measuring of any of the BICV within which a certain visual quality criterion is satisfied.
  i. According to some embodiments of the present invention, the measuring of any of the BICV can comprise displaying on an electronic screen to a user a target with spatial features oriented at a certain angle $\alpha$ and measuring a corresponding distance between the user and the target.
  ii. According to some embodiments of the present invention, the measuring of any of the BICV can further comprise displaying to a user a target with spatial detail at a different angle $\beta$, which can be perpendicular to angle $\alpha$, and measuring a corresponding distance between the user and the target.

iii. According to some embodiments of the present invention, the measuring of any of the BICV can comprise configuring a distance measurement circuitry included in the electronic device to perform measurements.

iv. According to some embodiments of the present invention, the measuring of any of the BICV can comprise using an external apparatus to perform measurements, such as a ruler, a rangefinder or other, or any combination of any of the above.

v. According to some embodiments of the present invention, the visual quality criterion can comprise a visual acuity criterion (e.g. resolving lines, letters, etc.), a contrast sensitivity criterion (e.g. distinguishing tones of gray), a color discrimination criterion (e.g. distinguishing colors), subjective clarity, or other, or any combination of any of the above.

e. Computing ocular refractive errors and power and addition of reading glasses from measured BICV, information about an object (such as color of a target), information about a user (such as age, gender, or others), or any other, or combination of any of the above.

f. Storing ocular refractive errors and power and addition of reading glasses from measured BICV, information about an object (such as color of a target), information about a user (such as age, gender, or others), or any other, or combination of any of the above.

BRIEF DESCRIPTION OF DRAWINGS

The following figures accompanying the detailed description below serve to further illustrate the nature of the present invention and its advantages.

DETAILED DESCRIPTION

The present invention is directed to computer-implemented systems and methods for interactively measuring ocular refractive errors, addition and power of reading glasses. The method is based on subjective, interactive measurements of distance between a user's head and an electronic device, specifically corresponding to any of the BICV. The present invention, in some embodiments thereof, provides systems and methods for allowing users to accurately measure refractive errors of their eyes, or other people's eyes with or without wearing optical correction.

Figure 1:
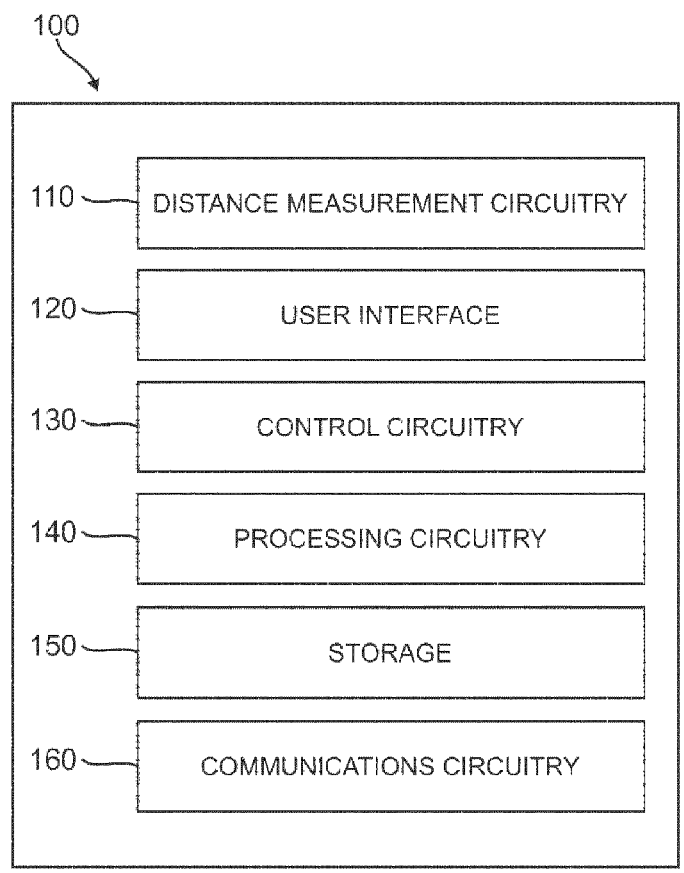
FIG. 1 is a schematic of an illustrative system for interactively measuring ocular refractive errors, addition and power of reading glasses in accordance with one embodiment of the invention.

FIG. 1 is a schematic of an illustrative, computer-implemented system for interactively measuring ocular refractive errors, addition and power of reading glasses in accordance with one embodiment of the invention. The system 100 can include distance measurement circuitry 110, user interface 120, control circuitry 130, processing circuitry 140, storage 150, and communications circuitry 160. In some embodiments, one or more of device's components can be combined or omitted. In some embodiments, system 100 can include additional components not included in FIG. 1, or a combination of any of the aforementioned components.

The system 100 can include any suitable type of electronic device with distance measurement circuitry used to measure the distance between the user's head and the device. For example, the system 100 can include any of the following devices equipped with a camera and a light sensor: a mobile phone, a tablet, a "smart" television set, a personal digital assistant (PDA), a laptop or desktop computer, a stand-alone camera or video-recorder, and any other suitable device. The electronic device included in system 100 is preferably, but not limited to, a portable device.

Distance measurement circuitry 110 can include any circuitry, emitters and detectors to measure the distance between the user's head or part of it and the electronic device. In some embodiments, distance measurement circuitry 110 can include a passive system comprising one or more cameras for capturing images of the user's head and circuitry to compute the distance between the user's head or part of it and the device from said images. In some embodiments, distance measurement circuitry 110 can include an active system comprising one or more emitters and detectors for measuring said distance.

User interface 120 can include any suitable mechanism for interaction with a user such as one or more screens, loudspeakers, tactile surfaces, keypads, microphones, or others, or any combination thereof. For example, in some embodiments, user interface 120 can include a tactile electronic screen for displaying targets and receiving user input.

Control circuitry 130 can include any type of circuitry, such as processors, micro-controllers and connections to control the functions, operations and performance of an electronic device included in system 100. Furthermore, control circuitry 130 can be electronically coupled with other components of the system 100, or any combination thereof. For example, in some embodiments of the invention, control circuitry 130 can send a control signal to user interface 120 to configure it for receiving input from a user or giving instructions to a user.

Processing circuitry 140 can include any type of circuitry, such as processors, micro-controllers and connections designed to process the data from distance measurement circuitry 110, user interface 120, and other components of the system 100, or any combination thereof for computing spherical and cylindrical errors of the eye, and power and addition of reading glasses. Furthermore, processing circuitry 140 can be electronically coupled with other components of the system 100, or any combination thereof. For example, in some embodiments of the invention, processing circuitry 140 can send a signal to control circuitry 130 to configure the user interface 120 or distance measurement circuitry 110.

Storage 150 can include one or more storage media, such as internal or external memory of any type, such as: HDD, SSD, RAM, ROM, EPROM, Flash EEPROM, flash memory card such as an SD (i.e. Secure Digital) card of CF (i.e.

Compact Flash) card, or any other type of memory suitable for the electronic device included in system 100.

Communications circuitry 160 can include any circuitry suitable to connect the electronic device included in system 100 to a communications network and transmit data using any suitable protocol such as, for example, Wi-Fi (e.g., 802.11 protocol), Bluetooth®, cellular protocol (e.g., GSM, GPRS, CDMA, EDGE, LTE), or any other communications protocol or any combination thereof.

Figure 2:
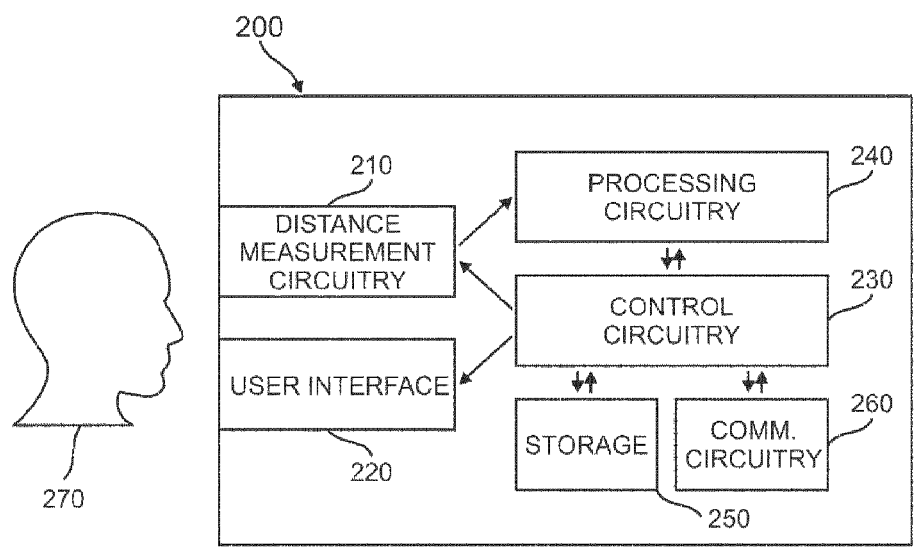
FIG. 2 is a block diagram of an illustrative electronic device for interactively measuring ocular refractive errors, addition and power of reading glasses in accordance with one embodiment of the invention where a camera is included in the distance measurement module and a screen is included in the user interface.

FIG. 2 is a block diagram of an illustrative electronic device 200 for interactively measuring ocular refractive errors, addition and power of reading glasses in accordance with one embodiment of the invention.

Electronic device 200 can be very similar to electronic device included in the system 100 shown in FIG. 1 and share descriptions of components of the latte. For example, electronic device 200 can also include storage 250 and communications circuitry 260, that can be substantially similar to respective components of electronic device in system 100; storage 150, and communications circuitry 160, or others, or any combination thereof.

Distance measurement circuitry 210 can be similar to distance measurement circuitry 110 and use any suitable technique or combination of techniques for measuring distance between a user's head 270 and electronic device 200.

User interface 220 can be connected to control circuitry 230 and processing circuitry 240. User interface (120; 220) can be configured to provide instructions to a user by means of a visual instruction message (see 304 in FIG. 3), or an audio message, or other user interface method, or any combination of the above methods. Furthermore, user interface (120; 220) can be configured to receive input from the user by means of touching or swiping a tactile screen, or typing on a keypad or keyboard, speaking into a microphone, performing a gesture detected by a camera, performing a gesture detected by a gyroscope or others or any combination of any of the above.

Control circuitry 230 can be similar to control circuitry 130, and processing circuitry 240 can be similar to processing circuitry 140. Processing circuitry 240 can use any suitable technique or combination of techniques for computing ocular refractive errors and power and addition of reading glasses from measurements of distance between a user's head or part of it 270 and electronic device 200 obtained from distance measurement circuitry 210, and user input obtained from user interface 220, both configured by signals from control circuitry 230.

For example, control circuitry 230 can configure the user interface 220 to instruct the user to slowly bring the electronic device 200 into proximity to the user's head 270, until the tactile screen 220 can only barely be read due to said proximity, corresponding to a near border of the interval of clear vision. Furthermore, control circuitry 230 can instruct the user (or another) to touch the tactile screen 220 to indicate said proximity. The processing circuitry 240 can then use this user input and the current measurement of distance between the user's head 270 and the electronic device 200 obtained from distance measurement circuitry 210 to measure dNP and pNP. As another example, user interface 220 can instruct the user to slowly move the electronic device 200 further away from the user's head 270, until the tactile screen 220 can only barely be read due to its distance from the head, corresponding to a far border of interval of clear vision. Furthermore, control circuitry 230 can instruct the user to touch the tactile screen 220 to indicate said proximity. The processing circuitry 240 can then use this user input and the current measurement of distance between the user's head 270 and the electronic device 200 obtained from distance measurement circuitry 210 to measure dPF and pFP. Furthermore, processing circuitry 240 can use any suitable technique or combination of techniques for computing the BICV and additional information, such as the user's age, gender, eye to be tested or other, or others, or any combination thereof.

In some embodiments, processing circuitry 240 can automatically detect the user's age, gender or eye to be tested from an image of the user's head 270 from a camera included in distance measurement circuitry 210. In some embodiments, processing circuitry 240 can obtain the user's age and gender by sending a signal to control circuitry 230 configuring the tactile screen included in the user interface 220 to prompt the user to input their age, gender, eye to be tested, or others, or any combination of any of the above.

In some embodiments of the invention, the control circuitry 230 can configure tactile screen included in the user interface 220 to display a target to aid the user in situating the electronic device 200 at any of the BICV.

Figure 3:
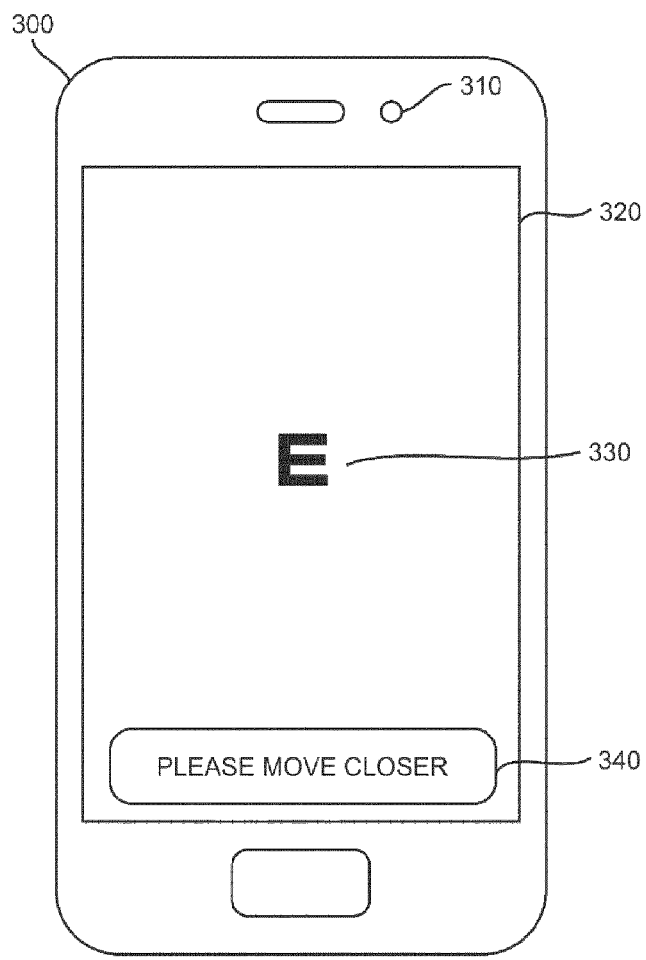
FIG. 3 is an example view of an illustrative screen of an electronic device for interactively measuring ocular refractive errors, addition and power of reading glasses in accordance with one embodiment of the invention.
Figure 3:
Figure 3:
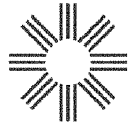
Figure 3:
Figure 3:
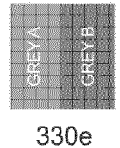
Figure 3:
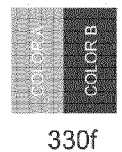
Figure 3:
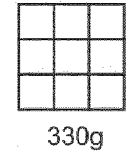
Figure 3:
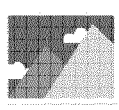

FIG. 3 is an example view of an illustrative screen of an electronic device 300 for interactively measuring ocular refractive errors in accordance with one embodiment of the invention where a target is displayed on a tactile screen included in the user interface.

Electronic device 300 can be substantially similar to device 100 shown in FIG. 1 and device 200 shown in FIG. 2 and share descriptions of components with either or both. For example, the electronic device 300 can include a camera in distance measurement circuitry 310 and a tactile screen in the user interface 320. In some embodiments the tactile screen included in the user interface 320 can be configured to show a target 330 to the user, including but not limited to the following types of targets; an optotype 330*a*, text 330*b*, a geometrical pattern 330*c,d*, a grey discrimination test 330*e*, a color discrimination test 330*f*, a spatial geometry test 330*g*, or a picture or movie 330*h* or any combination of any of the above.

In some embodiments the target 330 can be configured to change its characteristics depending on the measured distance between the users head 270 and electronic device 300. For example, target 330 can be configured to change size, shape, rotation, color, background color or other characteristics or any combination of any of the above as the distance between the user's head 270 and electronic device 300 changes.

In some embodiments the target 330 can be configured to change its characteristics depending on the user input from the user interface 320. For example, target 330 can be configured to change size, shape, rotation, color, background color or other characteristics, or any combination of any of the above as a result of user interaction with the electronic device 300 using the tactile screen 320 such as a swipe, tap, click, voice command or other gesture, or any combination of any of the above. Furthermore, in some embodiments the user interaction with user interface 320 can be performed using a keypad, keyboard, mouse, microphone, or any other interface method, or any combination of any of the above.

Figure 4:
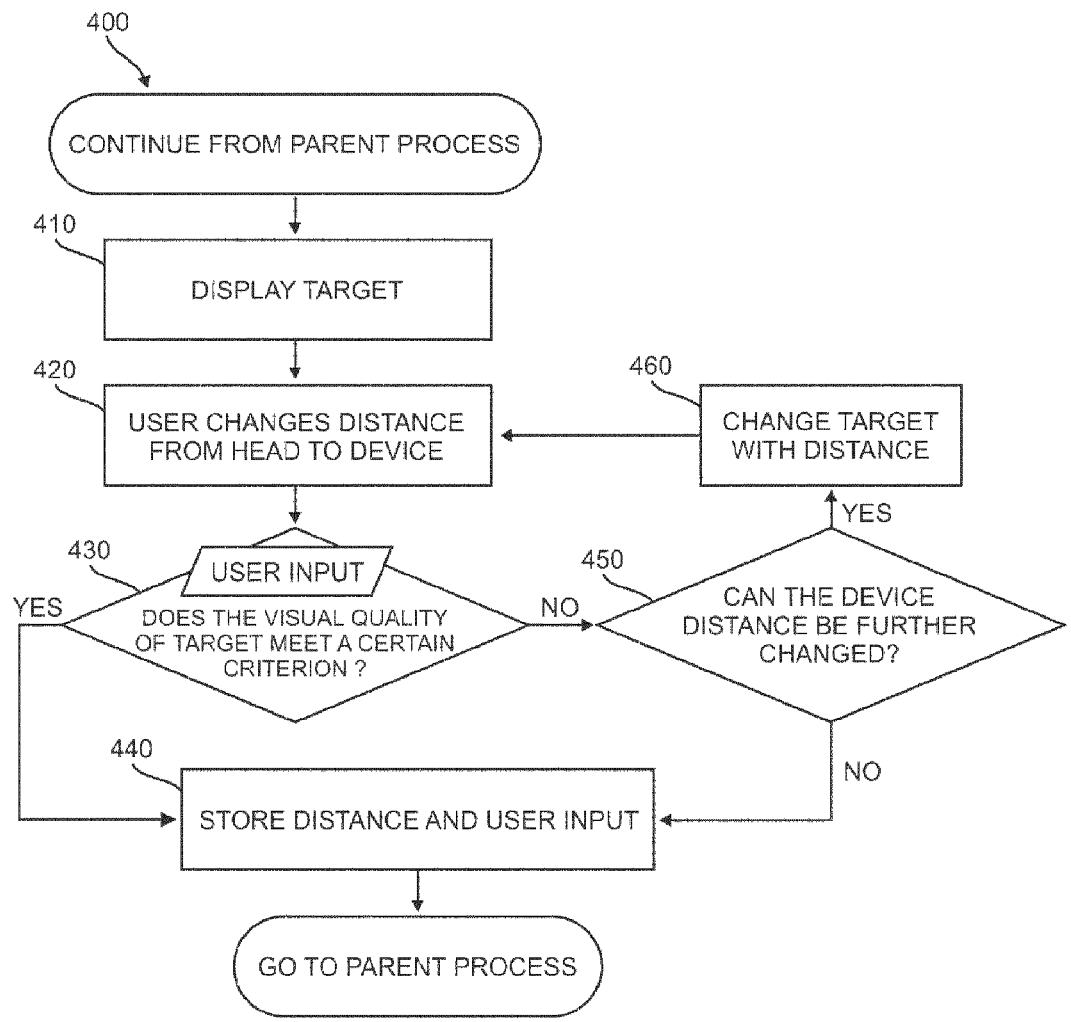
FIG. 4 is a flowchart of an illustrative sub-process for changing a target with distance between a head and electronic device in accordance with one embodiment of the invention.

FIG. 4 is a flowchart of an illustrative sub-process 400 for changing a target with distance between a head and electronic device in accordance with one embodiment of the invention. Sub-process 400 can consist of several steps. In some embodiments the order of steps of sub-process 400 can be changed or some steps can be omitted or repeated. Furthermore, sub-process 400 can be included in another process (parent process) as a sub-process.

Sub-process 400 can be performed by an electronic device (100; 200; 300) with distance measurement circuitry (110; 210; 310) and user interface (120; 220; 320), and one or more other components of the electronic device (100; 200; 300).

The first step of sub-process 400 can continue from a parent process and begin with block 410 where the user interface (120; 220; 320) can be configured to display a target 330 on a screen 320. For example, in one embodiment of the invention, said target can be an optotype 330*a*, or text 330*b*, or one or more parallel lines 330*c*, 330*d*, or one or more grey patches 330*e* or color patches 330*f*, or a geometrical pattern such as a grid 330*g*, or a picture 330*h*, or other type of target, or any combination of any of the above.

At block 420 a user can change the distance between the user's head 270 and electronic device (100; 200; 300). Furthermore, distance measurement circuitry (110; 210; 310) can send to processing circuitry (140; 240) a signal including a measurement of distance between a user's head 270 and electronic device (100; 200; 300). As previously indicated, distance measurement circuitry (110; 210; 310) can use any suitable technique or combination of techniques for measuring distance between a user's head 270 and electronic device. Furthermore, said distance between the user's head and the device can be measured using another method (such as a ruler or rangefinder) and input into user interface (120; 220; 320).

In some embodiments of the present invention, the change of the distance between the user's head 270 and electronic device can comprise holding the device in a user's hand and bringing it closer to the face or further away from the face.

In some embodiments of the present invention, the change of distance between the user's head 270 and electronic device can comprise situating a reflective surface, such as a mirror, in front of the electronic device (so that a reflection of a user's head 270 is within the field of view of the electronic device), and changing the distance between the device and a mirror, or the distance between said user's head or part of it 270 and a mirror, or any combination thereof.

In some embodiments of the present invention, the changing the distance between the user's head 270 and electronic device can comprise changing the distance by a third party, such as another person, another apparatus, or other, or any combination of any of the above.

At block 430, user interface can be configured to change characteristics of a target 330. For example, in one embodiment of the invention the distance measurement circuitry (110; 210; 310) can send to processing circuitry (140; 240) a signal including a measurement of distance between a user's head 270 and electronic device (100; 200; 300). The processing circuitry can use any technique or combination of techniques to process said signal and send a signal to control circuitry (130; 230), which in turn can configure the user interface (120; 220; 320) to change such characteristics of the target 330 such as size, shape, rotation, color, background color or other characteristics or other, or any combination of any of the above, in accordance with said distance between a user's head 270 and electronic device.

Block 440 can be a decision block where the user interface (120; 220; 320) can be configured to instruct the user to evaluate if a target 330 meets a certain visual quality criterion. For example, in one embodiment of the invention, said visual quality criterion can be a visual acuity criterion (e.g. being able to read optotypes (330*a*) or text (330*b*), or resolve two or more parallel lines (330*c, d*), or other, or any combination of any of the above). As another example, in one embodiment of the invention, said visual quality criterion can be a contrast sensitivity criterion (e.g. being able to distinguish grey patches (330*e*) or match grey patches) or a color discrimination criterion (e.g. being able to distinguish colors (330*f*) or match colors), or a spatial geometry criterion (e.g. being able to detect deformations in geometrical patterns (330*g*) such as warping of a grid) or recognize pictures or details in pictures (330*h*), or other criterion, or any combination of any of the above.

Furthermore, at the decision block 450 if user input to the user interface (120; 220; 320) indicates that a target 330 meets a certain visual quality criterion, the sub-process 400 can proceed to block 440.

On the other hand, at decision block 450 if user input to the user interface (120; 220; 320) indicates that a target 330 doesn't meet a certain visual quality criterion, process 400 can go to block 460, which can be a decision block. At block 450, which can be a decision block, if the distance between a user's head 270 and electronic device can be further changed, sub-process 400 can return to block 420. On the other hand, at block 450, if said distance can't be further changed (for example a user is not able to move the electronic device further away than arm distance), sub-process 400 can proceed to block 450.

At block 440 a distance between a user's head 270 and the electronic device (100; 200; 300) can be stored in storage (150; 250) along with, but not limited to user input data. Furthermore, at block 440 sub-process 400 can return to a parent process in which it can be included.

Figure 5:
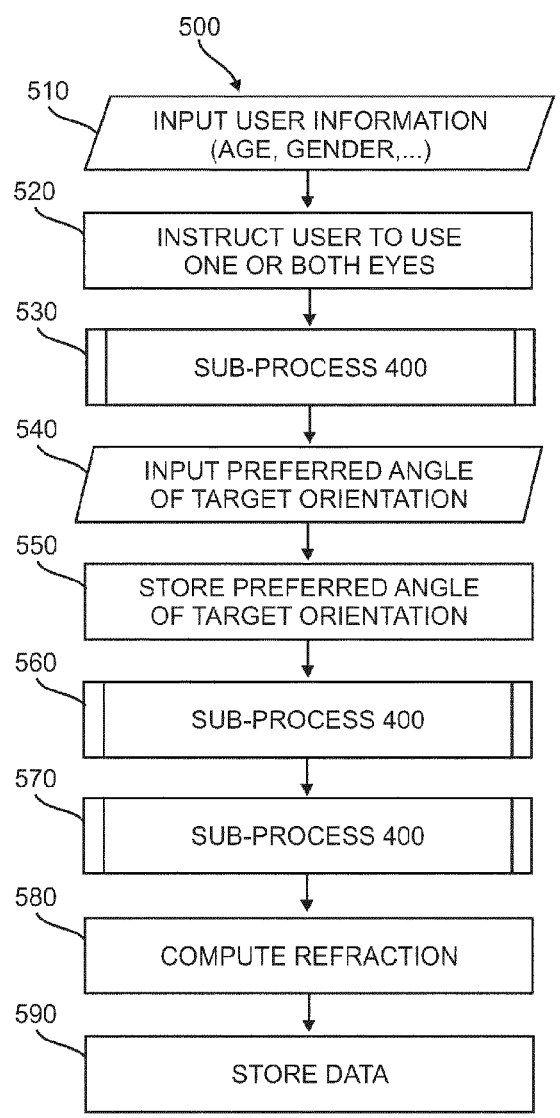
FIG. 5 is a flowchart of an illustrative process for interactively measuring ocular refractive errors, addition and power of reading glasses in accordance with one embodiment of the invention.

FIG. 5 is a flowchart of an illustrative process 500 for interactively measuring ocular refractive errors, addition and power of reading glasses in accordance with one embodiment of the invention. Process 500 can consist of several steps. In some embodiments the order of steps of process 500 can be changed or some steps can be omitted or repeated.

Process 500 can be performed by an electronic device (100; 200; 300) with distance measurement circuitry (110; 210; 310) and user interface (120; 220; 320), and one or more other components of the electronic device (100; 200; 300).

Process 500 can begin at block 510 where a user interface (120; 220; 320) of an electronic device (100; 200; 300) can be configured to receive user input information, such as age, gender, value of the sphero-cylindrical power of the ophthalmic or contact lenses already ported by the subject, vertex distance, or others or any combination thereof. For example, in one embodiment of the invention said information can be acquired by configuring the user interface (120; 220; 320) to prompt the user to input said information into the user interface using a tactile screen or voice recognition circuitry, or other, or any combination thereof. As another example, in one embodiment of the invention said information can be acquired automatically by means of detecting it from an image of a user's head 270 from a camera included in said user interface.

At block 520, user interface (120; 220; 320) can be configured to instruct a user to use one (left or right) eye or both eyes while interacting with electronic device (100; 200; 300).

At block 530 process 500 can include sub-process 400 (see FIG. 4). For example, in one embodiment of the invention, at the decision block 430 of sub-process 400 included at block 520 of process 500 a user can provide user input to user interface (120; 220; 320) indicating that visual quality of a target 330 meets a certain criterion corresponding to an electronic device (100; 200; 300) being situated at or in proximity to either far or near border of interval of clear vision BICV. At block 440 (see FIG. 4) of sub-process 400 included at block 530 of process 500, the distance between an electronic device (100; 200; 300) and a subject's head 270 can be stored in storage (150; 250).

At block 540 user interface (120; 220; 320) can be configured to display a new target and instruct a user to select a preferred angle of target orientation while interacting with electronic device (100; 200; 300). As an example, in one embodiment of the invention, the user interface (120; 220; 320) of an electronic device (100; 200; 300) situated in proximity of dFP (or pNP) can be configured to receive user input including a preferred angle of target orientation αdFP (or αpNP). In one embodiment of the invention, the user interface (120; 220; 320) can be configured to change a target 330 on a tactile screen 320 in response to user input such as touching or swiping a tactile screen, or typing on a keypad or keyboard, speaking into a microphone, performing a gesture to detected by a camera, performing a gesture detected by a gyroscope, or others or any combination of any of the above. As a further example, in one embodiment of the invention, user interface (120; 220; 320) can be configured to display a target 330 including, but not limited to a set of parallel lines on a tactile screen 320, and to receive user input from said tactile screen 320 and perform change of orientation of said target 320 by angle α dFP (or α pNP).

At block 550, a preferred angle of target orientation α dFP selected by a user at block 540 can be stored in storage (150; 250).

At block 560 process 500 can include sub-process 400 (see FIG. 4). At block 410, user interface (120; 220; 320) can be configured to display a new target 330 including, but not limited to a set of parallel lines on a tactile screen 320 oriented at angle α dFP (or αpNP). At decision block 430 of sub-process 400 included at block 560 of process 500 a user can provide user input to user interface (120; 220; 320) indicating that visual quality of said target 330 meets a certain criterion corresponding to an electronic device (100; 200; 300) being situated at or in proximity of dFP (or pNP). At block 440 of sub-process 400 dFP (or pNP), can be stored in storage (150; 250).

At block 570 process 500 can include sub-process 400 (see FIG. 4). At block 410, user interface (120; 220; 320) can be configured to display a new target 330 including, but not limited to a set of parallel lines on a tactile screen 320 oriented at angle αpFP=αdFP+90° (or αdNP=αpNP−90°). At decision block 430 of sub-process 400 included at block 570 of process 500 a user can provide user input to user interface (120; 220; 320) indicating that visual quality of said target 330 meets a certain criterion corresponding to an electronic device (100; 200; 300) being situated at or in proximity of pFP (or dNP). At block 440 of sub-process 400 pFP (or dNP) can be stored in storage (150; 250).

At block 580 processing circuitry (140; 240) can use any technique or combination of techniques to compute ocular refractive errors such as, but not limited to, sphere (SPH), cylinder (CYL) and axis (AXS) from dFP, pFP, αdFP αpFP, dNP, pNP, αdNP, or αpNP or others, or any combination of any of the above.

In one embodiment of the invention, AXS can be calculated from αdFP and αpFP using, for example, the following equations:

$$AXS = 90° - \alpha pFP \text{ when } 0° < \alpha dFP < 90°; \text{ or}$$

$$AXS = 270° - \alpha dFP \text{ otherwise;} \qquad \text{Eq. 1}$$

$$\text{and } \alpha dFP = \alpha pFP - 90°. \qquad \text{Eq. 2}$$

Furthermore, AXS can be calculated from αdNP and αpNP using, for example, the following equations:

$$AXS = 90° - \alpha dNP \text{ when } \alpha dNP < 90°; \text{ or}$$

$$AXS = 270° - \alpha dNP \text{ otherwise;} \qquad \text{Eq. 3}$$

$$\text{and } \alpha dNP = \alpha pNP - 90°. \qquad \text{Eq. 4}$$

where αdNP, αpNP, αdFP, and αpFP are expressed in units of degrees from 1° to 180°.

SPH and CYL can be calculated from dFP, pFP using, for example, the following equations:

$$SPH = -1/dFP + K. \qquad \text{Eq. 5}$$

$$CYL = -(1/pFP - 1/dFP), \qquad \text{Eq. 6}$$

where parameter K depends on target and background color. In a case of a black background, K=0 D, K>0 D and K<0 D for white, blue and red targets, respectively. The specific value of K depends on an emission spectrum of a physical target.

In one embodiment of the invention, SPH and CYL can be also calculated from dNP, pNP using, for example, the following equations:

$$SPH = AA - 1/dNP + K. \qquad \text{Eq. 7}$$

$$CYL = -(1/pNP - 1/dNP), \qquad \text{Eq. 8}$$

where AA value can depend on AGE as:

$$AA = 15.6 - 0.3 * AGE \text{ when } AGE <= 52 \text{ years; or}$$

$$AA = 0 \text{ D otherwise.} \qquad \text{Eq. 9}$$

Values of dFP, pFP, dNP, pNP can be expressed in meters and K in diopters. AGE can be expressed in years.

Furthermore, at block 580 processing circuitry (140; 240) can use any technique or combination of techniques to compute power of reading glasses (P) from dNP or pNP, or other parameters, or any combination thereof. For example, in one embodiment of the invention, the power of the reading glasses P can be calculated as:

$$P = 3 \text{ D} - E (1/((dNP+pNP)/2)+K), \text{ when } E(1/((dNP+pNP)/2)+K) < 3 \text{ D}$$

$$P = 0 \text{ D otherwise.} \qquad \text{Eq. 10}$$

where P can be expressed in diopters and E can be a constant value between 0 and 1.

As described previously, at block 520 of process 500, user interface (120; 220; 320) can be configured to instruct a user to use one (left or right) eye or both eyes while interacting with electronic device (100; 200; 300). As an example, in one embodiment of the invention, at block 410 (see FIG. 4) of sub-process 400 included at block 530 of process 500, user interface (120; 220; 320) can be configured to display a target 330 including, but not limited to a text (330*b*). At block 440 of sub-process 400 a near point distance NP can be stored in storage (150; 250) and the power P of the reading glasses can be calculated as:

$$P = 3 \text{ D} - E(1/NP + K), \text{ when } E(1/NP + K) < 3 \text{ D}$$

$$P = 0 \text{ D otherwise.} \qquad \text{Eq. 11}$$

where NP can be expressed in meters.

In one embodiment of the invention, addition of reading glasses (ADD) can be calculated using the following equations:

$$ADD = P - (SPH + CYL/2) \text{ when } P > (SPH + CYL/2); \text{ or}$$

$$ADD = 0 \text{ D otherwise.} \qquad \text{Eq. 12}$$

Eq. 1-12 correspond to corneal-plane refraction.

Furthermore, at block 580 of process 500 processing circuitry (140; 240) included in an electronic device (100; 200; 300) can use any suitable technique or combination of techniques to compute spectacle-plane refraction or power of reading glasses from corneal-plane refraction from dFP, pFP, dNP, pNP, FP, NP, vertex distance (VD) or others, or any combination thereof. VD depends on the type of correction (usually 0.0 m for contact lenses and 0.014 m for glasses).

At block 590 parameters such as, but not limited to, SPH, CYL, AXS, FP, NP, P, ADD, dFP, pFP, αdFP αpFP, dNP, pNP, αdNP, αpNP, VD, user input, or others, or any combination of any of the above can be saved in storage (150; 250).

The invention claimed is:

1. A computer-implemented method for interactively measuring ocular refractive errors, addition and power of reading glasses of a user of an electronic device comprising:
   displaying a target on an electronic screen of the electronic device,
   receiving a first input from the user and changing spatial characteristics of the target according to said user input,
   receiving a second input from the user indicating that the electronic screen of the electronic device is positioned at one of the borders of the interval of clear vision (BICV) where a visual quality of the target satisfies a certain visual quality criterion, wherein the certain visual quality criterion is a contrast sensitivity criterion, a color discrimination criterion, subjective clarity, or a combination thereof;
   measuring at least a distance between the user's head or part of the user's head and the electronic screen using the second input;
   computing at least one parameter of refraction selected from a first group consisting of: cylinder (CYL) axis (AXS) and power of the reading glasses (P), at least from said measured distance; or selected from a second group consisting of: a sphere (SPH) and addition (ADD), from at least said measured distance and from user's age (AGE).

2. The computer-implemented method of claim 1, wherein the displaying the target on the electronic screen of the electronic device comprises changing characteristics of said target size, orientation, position or color being able to change independent of each other with distance between said user and said electronic device.

3. The computer-implemented method according to claim 1, where said target on the electronic screen of the electronic device comprises:
   a single letter, optotype or a group thereof,
   a text,
   a geometrical pattern,
   a color or grayscale pattern,
   a repetitive pattern such as a grid,
   a picture or movie, and
   other spatial stimuli or any combination of any of the above.

4. The computer-implemented method according to claim 1, wherein said changing characteristics of the target according to said user input comprises rotation, translation, changing size, changing shape, changing color, or others, or any combination thereof.

5. The computer-implemented method according to claim 1, further comprising:
   interactively changing a rotation of the target on the electronic screen by the user to a preferred angle of target orientation wherein a visual quality of an image of said target satisfies a certain visual quality criterion;
   measuring a first distance between the electronic screen and the user's head or part of it;
   changing the target so that the target includes at least one line oriented perpendicularly to said preferred angle of target orientation and measuring a second distance between said electronic screen and the user's head;
   computing at least one parameter of refraction from the first and second distances, preferred angle of target orientation, user's AGE, spectral color characteristics of said target, or other parameters, or any combination thereof.

6. The computer-implemented method according to claim 5, wherein said first distance is computed from a mathematical relation between the user's age and said second distance.

7. The computer-implemented method according to claim 1, wherein a preferred angle of target orientation is found by physically rotating the screen or the stimuli on the screen of the electronic device around the user's line of sight.

8. The computer-implemented method according to claim 1, wherein a preferred angle of target orientation is computed from an image of the user's head or part of the user's head which is rotated with respect to the screen of the electronic device.

9. The computer-implemented method according to claim 1, wherein a reflective surface is placed between the user's eye of a user's head or part of the user's head and said screen of the electronic device to change the optical path length of light travelling from said target to said user's eye.

10. The computer-implemented method according to claim 1, wherein at least one of said at least one parameter of refraction is recalculated from a mathematical relation between said parameter and vertex distance (VD) from corneal-plane to spectacle-plane, or vice-versa.

11. The computer-implemented method according to claim 1, wherein said user's age (AGE) is obtained from one of the following methods:
   inputting AGE or date of birth into a user interface by the user or remotely from a data base of the electronic device,
   detecting AGE from an image of the user's head or part of the user's head using an age detection algorithm;
   or any combination thereof.

12. A computer program product comprising non-transitory computer-readable medium having computer code instructions stored thereon, that when executed by a processor of a device, cause the processor to carry out a method according to claim 1.

13. A system included in an electronic device for interactively measuring ocular refractive errors, addition and power of reading glasses of a user comprising:
   a distance measurement circuitry configured to measure a distance between a user's head or part of the user's head and the electronic screen of the electronic device based on a user input;
   a user interface configured to give instructions to the user and receiving the user input;
   an electronic screen for displaying and changing a target;

a processing circuitry configured to compute at least one parameter of refraction;

a storage configured to save the at least one parameter of refraction in a memory of the electronic device, wherein the user input for the distance measurement circuitry indicates that the electronic screen of the electronic device is positioned at one of the borders of the interval of clear vision (BICV) where a visual quality of the target satisfies a certain visual quality criterion;

wherein the certain visual quality criterion is a contrast sensitivity criterion, a color discrimination criterion, subjective clarity, or a combination thereof;

wherein the at least one computed parameter of refraction is selected from a first group consisting of: cylinder (CYL), axis (AXS) and power of the reading glasses (P), from at least said measured distance; or selected from a second group consisting of: sphere (SPH), and addition (ADD), from at least said measured distance and from user's age.

14. The system according to claim 13, wherein the distance measurement circuitryand user interface of the electronic device is further configured to:

measure a rotation of the device with respect to an axis such as, but not limited to a line of sight between the user and said electronic device;

measure a rotation or tilt of the user's head or part of it with respect to said axis.

15. The system according to claim 13, wherein the user interface further comprises:

a speaker, a microphone, voice recognition circuitry, or any combination thereof.

16. A device comprising the system according to claim 13, wherein the device is:

a mobile phone;

a tablet;

a smart television;

a personal digital assistant;

a laptop computer;

a desktop computer;

a stand-alone camera;

a game console; or a video-recorder.

17. The system according to claim 13, wherein a communications circuitry configured to transmit the at least one parameter of refraction to and from a network.

* * * * *